United States Patent
Edwards et al.

(10) Patent No.: US 7,220,772 B2
(45) Date of Patent: *May 22, 2007

(54) PYRAZOLE DERIVATIVES

(75) Inventors: Paul John Edwards, Sandwich (GB); Lyn Howard Jones, Sandwich (GB); Charles Eric Mowbray, Sandwich (GB); Paul Anthony Stupple, Sandwich (GB); Isabelle Tran, Sandwich (GB)

(73) Assignee: Pfizer, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/657,033

(22) Filed: Sep. 5, 2003

(65) Prior Publication Data

US 2005/0054707 A1    Mar. 10, 2005

(51) Int. Cl.
*A61K 31/4152* (2006.01)
*C07D 231/18* (2006.01)

(52) U.S. Cl. .................................. 514/407; 548/370.1
(58) Field of Classification Search ................ 514/407; 548/370.1
See application file for complete search history.

(56) References Cited

U.S. PATENT DOCUMENTS 6,586,430 B1    7/2003    Armour

FOREIGN PATENT DOCUMENTS

| GB | 0223234.6 | 6/2003 |
|---|---|---|
| WO | WO 91/11172 | 8/1991 |
| WO | WO 94/02518 | 2/1994 |
| WO | WO 98/55148 | 12/1998 |
| WO | WO 02/04424 A1 | 1/2002 |
| WO | WO 02/30907 A1 | 4/2002 |
| WO | WO 02/085860 | 10/2002 |

OTHER PUBLICATIONS

Stanovnic, et al., Science of Synthesis, 2002, 15-225, vol. 12.
Berge, et al., "Pharmaceutical Salts," *Journal of Pharmaceutical Sciences*, 1977, 1-19, vol. 66, No. 1.
Bighley, et al., "Salt Forms of Drugs and Absorption," *Encyclopedia of Pharmaceutical Technology, Marcel Dekker Inc. New York*, 1996, pp. 453-497, vol. 13.
Bundgaard, H., *Design of Prodrugs*, 1985, Elsevier Science Publishers, Amsterdam, New York, Oxford.
Carey, et al., "Part A: Structure and Mechanisms," *Advanced Organic Chemistry*, 3rd Edition, Plenum Press, New York, London, 1990.
Ferres, et. al. "Pro-Drugs ov β-Lactam Antibiotics," *Drugs of Today* 1983, 499-538, vol. 19, No. 9.
Genin, M. et al., "Novel 1,5-Diphenylpyrazole Nonnucleoside HIV-1 Reverse Transcriptase Inhibitors with Enhanced Activity Versus The Delavirdine-Resistant P236L Mutant: Lead Identification and SAR of 3- and 4-Substituted Derivatives," *Journal of Medicinal Chemestry*, 2000, vol. 43, p. 1034-1040.
Greene, T. *Protective Groups in Organic Synthesis* 2nd Edition 1991, John Wiley & Sons, Inc., New York, Chichester, Brisbane, Toronto, Singapore.
Hajimorad, et al., "Some Observations On The Binding Properties Of Alfalfa Mosaic Virus To Polystyrene And Its Significance To Indirect ELISA," *Archives of Virology*, 1991, pp. 219-235, vol. 117.
Katritzky, et al. "The Structure, Reactions, Synthesis and Uses of Heterocyclic Compounds," *Comprehensive Heterocyclic Chemistry* vol. 1-11, Pergamon Press, Oxford, New York, Toronto, Sydney, Paris, Frankfurt, 1984.

*Primary Examiner*—Taofiq Solola
(74) *Attorney, Agent, or Firm*—Keith D. Hutchinson; Bryan C. Zielinski

(57) ABSTRACT

This invention relates to pyrazole derivatives of formula (I)

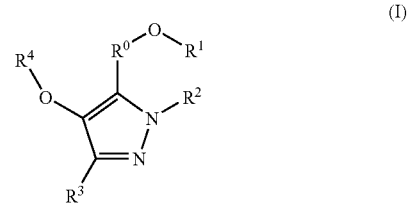

(I)

or pharmaceutically acceptable salts, solvates or derivative thereof, wherein $R^1$ to $R^4$ are defined in the description, and to processes for the preparation thereof, intermediates used in their preparation of, compositions containing them and the uses of such derivatives. The compounds of the present invention bind to the enzyme reverse transcriptase and are modulators, especially inhibitors thereof. As such the compounds of the present invention are useful in the treatment of a variety of disorders including those in which the inhibition of reverse transcriptase is implicated. Disorders of interest include those caused by Human Immunodeficiency Virus (HIV) and genetically related retroviruses, such as Acquired Immune Deficiency Syndrome (AIDS).

6 Claims, No Drawings

PYRAZOLE DERIVATIVES

The present patent application claims priority to United Kingdom provisional application no. 0223234.6 on Oct. 7, 2002 and U.S. Ser. No. 60/432,781, filed Dec. 11, 2002, which is hereby incorporated by reference in its entirety.

This invention relates to pyrazole derivatives, to their use in medicine, to compositions containing them, to processes for their preparation and to intermediates used in such processes.

BACKGROUND OF THE INVENTION

Reverse transcriptase is implicated in the infectious lifecycle of Human Immunodeficiency Virus (HIV). Compounds which interfere with the function of this enzyme have shown utility in the treatment of conditions caused by HIV and genetically related retroviruses, such as Acquired Immune Deficiency Syndrome (AIDS). There is a constant need to provide new and better modulators, especially inhibitors, of HIV reverse transcriptase, since the virus is able to mutate, becoming resistant to the effects of known modulators.

Antiviral activity is ascribed to a class of N(hydroxyethyl) pyrazole derivatives in U.S. Pat. No. 3,303,200. A number of pyrazoles are disclosed as reverse transcriptase inhibitors, including: a class of N-phenylpyrazoles (*J. Med. Chem.*, 2000, 43, 1034); a class of C and S linked aryl pyrazoles (WO02/04424); and a class of O and S linked aryl pyrazoles, the O and S aryl link being adjacent to the nitrogen atom (WO02/30907).

SUMMARY OF INVENTION

According to the present invention there is provided a compound of formula (I)

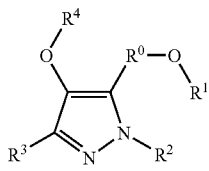

(I)

or a pharmaceutically acceptable salt, solvate or derivative thereof, wherein:

$R^0$ is absent or $C_1$–$C_6$ alkylene;

$R^1$ is phenyl substituted by —$SO_yR^5$, —($C_1$–$C_6$ alkylene)-$SO_yR^5$, —$SO_yCF_3$, —($C_1$–$C_6$ alkylene)-$SO_yCF_3$, —$CO_2R^5$, —($C_0$–$C_6$ alkylene)-$CO_2R^5$, $OCF_3$, a five or six-membered aromatic heterocyclic group containing (i) from 1 to 4 nitrogen heteroatom(s) or (ii) 1 or 2 nitrogen heteroatom(s) and 1 oxygen or 1 sulphur heteroatom (said heterocyclic group being optionally substituted by halo, oxo, —CN, —$COR^5$, —$CO_2R^5$, —$CONR^5R^5$, —$SO_yR^5$, —$SO_yCF_3$, —$SO_2NR^5R^5$, —$NR^5SO_2R^5$, —$OR^5$, —$OCF_3$, —$NR^5R^5$, —($C_1$–$C_6$ alkylene)-$NR^5R^5$, $C_1$–$C_6$ alkyl, fluoro($C_1$–$C_6$)alkyl or $C_3$–$C_7$ cycloalkyl), said phenyl being optionally additionally substituted by halo, —CN, —$COR^5$, —$CONR^5R^5$, —$SO_2NR^5R^5$, —$NR^5SO_2R^5$, —$OR^5$, —$NR^5R^5$, —($C_1$–$C_6$ alkylene)-$NR^5R^5$, $C_1$–$C_6$ alkyl, halo($C_1$–$C_6$)alkyl or $C_3$–$C_7$ cycloalkyl; or, when $R^0$ is $C_1$–$C_6$ alkylene, $R^1$ may also be a five or six-membered aromatic heterocyclic group containing (i) from 1 to 4 nitrogen heteroatom(s) or (ii) 1 or 2 nitrogen heteroatom(s) and 1 oxygen or 1 sulphur heteroatom or (iii) 1 or 2 oxygen or sulphur heteroatom(s), said heterocyclic group being optionally substituted by halo, oxo, —CN, —$COR^5$, —$CONR^5R^5$, —$SO_2NR^5R^5$, —$NR^5SO_2R^5$, —$OR^5$, —$OR^{11}$, —$NR^5R^5$, —($C_1$–$C_6$ alkylene)-$NR^5R^5$, $R^7$ or $R^{11}$;

$R^2$ is H, $C_1$–$C_6$ alkyl, $C_3$–$C_6$ alkenyl, $C_3$–$C_6$ alkynyl, $C_3$–$C_7$ cycloalkyl, $C_3$–$C_7$ cycloalkenyl, phenyl, benzyl, $R^8$ or $R^9$, said $C_1$–$C_6$ alkyl, $C_3$–$C_7$ cycloalkyl, phenyl and benzyl being optionally substituted by halo, —$OR^5$, —$OR^{10}$, —CN, —$CO_2R^7$, —$OCONR^5R^5$, —$CONR^5R^5$, —C(=$NR^5$)$NR^5OR^5$, —$CONR^5NR^5R^5$, —$NR^6R^6$, —$NR^5R^{10}$, —$NR^5COR^5$, —$NR^5COR^8$, —$NR^5COR^{10}$, —$NR^5CO_2R^5$, —$NR^5CONR^5R^5$, —$SO_2NR^5R^5$, —$NR^5SO_2R^5$, —$NR^5SO_2NR^5R^5$, $R^8$ or $R^9$;

$R^3$ is H, $C_1$–$C_6$ alkyl, $C_3$–$C_7$ cycloalkyl, phenyl, benzyl, halo, —CN, —$OR^7$, —$CO_2R^5$, —$CONR^5R^5$, $R^8$ or $R^9$, said $C_1$–$C_6$ alkyl, $C_3$–$C_7$ cycloalkyl, phenyl and benzyl being optionally substituted by halo, —CN, —$OR^5$, —$CO_2R^5$, —$CONR^5R^5$, —$OCONR^5R^5$, —$NR^5CO_2R^5$, —$NR^6R^6$, —$NR^5COR^5$, —$SO_2NR^5R^5$, —$NR^5CONR^5R^5$, —$NR^5SO_2R^5$, $R^8$ or $R^9$;

$R^4$ is phenyl, naphthyl or pyridyl, each being optionally substituted by $R^8$, halo, —CN, $C_1$–$C_6$ alkyl, $C_1$–$C_6$ haloalkyl, $C_3$–$C_7$ cycloalkyl, $C_1$–$C_6$ alkoxy, —$CONR^5R^5$, $OR^{11}$, $SO_xR^6$, O—($C_1$–$C_6$ alkylene)-$CONR^5R^5$, O—($C_1$–$C_6$ alkylene)-$NR^5R^5$, or O—($C_1$–$C_6$ alkylene)-$OR^6$;

each $R^5$ is independently either H, $C_1$–$C_6$ alkyl or $C_3$–$C_7$ cycloalkyl or, when two $R^5$ groups are attached to the same nitrogen atom, those two groups taken together with the nitrogen atom to which they are attached represent azetidinyl, pyrrolidinyl, piperidinyl, homopiperidinyl, piperazinyl, homopiperazinyl or morpholinyl, said azetidinyl, pyrrolidinyl, piperidinyl, homopiperidinyl, piperazinyl, homopiperazinyl and morpholinyl being optionally substituted by $C_1$–$C_6$ alkyl or $C_3$–$C_7$ cycloalkyl;

each $R^6$ is independently either H, $C_1$–$C_6$ alkyl or $C_3$–$C_7$ cycloalkyl;

$R^7$ is $C_1$–$C_6$ alkyl or $C_3$–$C_7$ cycloalkyl;

$R^8$ is a five or six-membered, aromatic heterocyclic group containing (i) from 1 to 4 nitrogen heteroatom(s) or (ii) 1 or 2 nitrogen heteroatom(s) and 1 oxygen or 1 sulphur heteroatom or (iii) 1 or 2 oxygen or sulphur heteroatom(s), said heterocyclic group being optionally substituted by halo, oxo, —CN, —$COR^5$, —$CONR^5R^5$, —$SO_2NR^5R^5$, —$NR^5SO_2R^5$, —$OR^5$, —$NR^5R^5$, —($C_1$–$C_6$ alkylene)-$NR^5R^5$, $C_1$–$C_6$ alkyl, fluoro($C_1$–$C_6$) alkyl or $C_3$–$C_7$ cycloalkyl;

$R^9$ is a four to seven-membered, saturated or partially unsaturated heterocyclic group containing (i) 1 or 2 nitrogen heteroatom(s) or (ii) 1 nitrogen heteroatom and 1 oxygen or 1 sulphur heteroatom or (iii) 1 oxygen or sulphur heteroatom, said heterocyclic group being optionally substituted by oxo, $C_1$–$C_6$ alkyl, $C_3$–$C_7$ cycloalkyl, —$SO_2R^5$, —$CONR^5R^5$, —$COOR^5$, —CO—($C_1$–$C_6$ alkylene)-$OR^5$ or —$COR^5$ and optionally substituted on a carbon atom which is not adjacent to a heteroatom by halo, —$OR^5$, —$NR^5R^5$, —$NR^5COR^5$, —$NR^5COOR^5$, —$NR^5CONR^5R^5$, —$NR^5SO_2R^5$ or —CN;

$R^{10}$ is $C_1$–$C_6$ alkyl substituted by $R^8$, $R^9$, —$OR^5$, —$CONR^5R^5$, —$NR^5COR^5$ or —$NR^5R^5$;

$R^{11}$ is phenyl optionally substituted by halo, —CN, —$COR^5$, —$CONR^5R^5$, —$SO_2NR^5R^5$, —$NR^5SO_2R^5$, —$OR^5$, —$NR^5R^5$, —($C_1$–$C_6$ alkylene)-$NR^5R^5$, $C_1$–$C_6$ alkyl, halo($C_1$–$C_6$)alkyl or $C_3$–$C_7$ cycloalkyl; and x and y are independently 0, 1 or 2.

DETAILED DESCRIPTION OF THE INVENTION

In the above definitions, halo means fluoro, chloro, bromo or iodo. Unless otherwise stated, alkyl, alkenyl, alkynyl, alkylene and alkoxy groups containing the requisite number of carbon atoms can be unbranched or branched chain. Examples of alkyl include methyl, ethyl, n-propyl, i-propyl, n-butyl, i-butyl, sec-butyl and t-butyl. Examples of alkenyl include ethenyl, propen-1-yl, propen-2-yl, propen-3-yl, 1-buten-1-yl, 1-buten-2-yl, 1-buten-3-yl, 1-buten-4-yl, 2-buten-1-yl, 2-buten-2-yl, 2-methylpropen-1-yl or 2-methylpropen-3-yl. Examples of alkynyl include ethynyl, propyn-1-yl, propyn-3-yl, 1-butyn-1-yl, 1-butyn-3-yl, 1-butyn-4-yl, 2-butyn-1-yl. Examples of alkylene include methylene, 1,1-ethylene, 1,2-ethylene, 1,1-propylene, 1,2-propylene, 2,2-propylene and 1,3-propylene. Examples of alkoxy include methoxy, ethoxy, n-propoxy, i-propoxy, n-butoxy, i-butoxy, sec-butoxy and t-butoxy. Examples of cycloalkyl include cyclopropyl, cyclobutyl, cyclopentyl, cyclohexyl and cycloheptyl. Where a heterocyclic group $R^1$, $R^8$ or $R^9$ is attached to an oxygen, sulphur or nitrogen heteroatom the heterocyclic group $R^1$, $R^8$ or $R^9$ must be linked through a ring carbon atom.

The pharmaceutically acceptable salts of the compounds of formula (I) include the acid addition and the base salts thereof.

Suitable acid addition salts are formed from acids which form non-toxic salts and examples are the hydrochloride, hydrobromide, hydroiodide, chloride, bromide, iodide, sulphate, bisulphate, nitrate, phosphate, hydrogen phosphate, acetate, fumarate, pamoate, aspartate, besylate, carbonate, bicarbonate/, camsylate, D and L-lactate, D and L-tartrate, esylate, mesylate, malonate, orotate, gluceptate, methylsulphate, stearate, glucuronate, 2-napsylate, tosylate, hibenzate, nicotinate, isethionate, malate, maleate, citrate, gluconate, succinate, saccharate, benzoate, esylate, and pamoate salts.

Suitable base salts are formed from bases which form non-toxic salts and examples are the sodium, potassium, aluminium, calcium, magnesium, zinc, choline, diolamine, olamine, arginine, glycine, tromethamine, benzathine, lysine, meglumine and diethylamine salts.

For reviews on suitable salts see Berge et al, J. Pharm. Sci., 66, 1–19, 1977 and Bighley et al., Encyclopedia of Pharmaceutical Technology, Marcel Dekker Inc, New York, 1996, Vol 13, pp453–497.

The pharmaceutically acceptable solvates of the compounds of formula (I) include the hydrates thereof.

The compound of formula (I) may be modified to provide pharmaceutically acceptable derivatives thereof at any of the functional groups in the compound. Examples of such derivatives are described in: Drugs of Today, Volume 19, Number 9, 1983, pp 499–538; Topics in Chemistry, Chapter 31, pp 306–316; and in "Design of Prodrugs" by H. Bundgaard, Elsevier, 1985, Chapter 1 (the disclosures in which documents are incorporated herein by reference) and include: esters, carbonate esters, hemi-esters, phosphate esters, nitro esters, sulfate esters, sulfoxides, amides, sulphonamides, carbamates, azo-compounds, phosphamides, glycosides, ethers, acetals and ketals.

The invention encompasses all isomers of the compound of formula (I) and pharmaceutically acceptable salts, solvates or derivatives thereof, including all geometric, tautomeric and optical forms, and mixtures thereof (e.g. racemic mixtures).

Separation of diastereoisomers may be achieved by conventional techniques, e.g. by fractional crystallisation, chromatography or high performance liquid chromatography (HPLC) of a stereoisomeric mixture of compounds. An individual enantiomer of a compound may also be prepared from a corresponding optically pure intermediate or by resolution, such as by HPLC of the corresponding racemate using a suitable chiral support, or by fractional crystallisation of the diastereoisomeric salts formed by reaction of the corresponding racemate with a suitable optically active acid or base, as appropriate.

The compound of formula (I) and pharmaceutically acceptable salts, solvates or derivatives thereof may have the ability to crystallize in more than one form, a characteristic known as polymorphism, and all such polymorphic forms ("polymorphs") are encompassed within the scope of the invention. Polymorphism generally can occur as a response to changes in temperature or pressure or both, and can also result from variations in the crystallization process. Polymorphs can be distinguished by various physical characteristics, and typically the x-ray diffraction patterns, solubility behaviour, and melting point of the compound are used to distinguish polymorphs.

Compounds of formula (I), pharmaceutically acceptable salts, solvates and derivatives thereof, isomers thereof, and polymorphs thereof, are hereinafter referred to as the compounds of the invention.

Preferred compounds of the invention are the compounds of formula (I) and pharmaceutically acceptable salts and solvates thereof.

Preferably, $R^0$ is $C_1$–$C_6$ alkylene.

Preferably, $R^0$ is $C_1$–$C_3$ alkylene.

Preferably, $R^0$ is ethylene.

Preferably, $R^1$ is phenyl substituted by —$SO_yR^5$, ($C_1$–$C_6$ alkylene)-$SO_yR^5$, —$SO_yCF_3$, —($C_1$–$C_6$ alkylene)-$SO_yCF_3$, —$CO_2R^5$, —($C_0$–$C_6$ alkylene)-$CO_2R^5$ or $OCF_3$, a five or six-membered aromatic heterocyclic group containing (i) from 1 to 4 nitrogen heteroatom(s) or (ii) 1 or 2 nitrogen heteroatom(s) and 1 oxygen or 1 sulphur heteroatom (said heterocyclic group being optionally substituted by halo, oxo, —CN, —$COR^5$, —$CO_2R^5$, —$CONR^5R^5$, —$SO_yR^5$, —$SO_yCF_3$, —$SO_2NR^5R^5$, —$NR^5SO_2R^5$, —$OR^5$, —$OCF_3$, —$NR^5R^5$, —($C_1$–$C_6$ alkylene)-$NR^5R^5$, $C_1$–$C_6$ alkyl, fluoro ($C_1$–$C_6$)alkyl or $C_3$–$C_7$ cycloalkylor), said phenyl being optionally additionally substituted by halo, —CN, —$COR^5$, —$CONR^5R^5$, —$SO_2NR^5R^5$, —$NR^5SO_2R^5$, —$OR^5$, —$NR^5R^5$, —($C_1$–$C_6$ alkylene)-$NR^5R^5$, $C_1$–$C_6$ alkyl, halo ($C_1$–$C_6$)alkyl or $C_3$–$C_7$ cycloalkyl.

Preferably, $R^1$ is phenyl substituted by —$SO_yR^5$, ($C_1$–$C_6$ alkylene)-$SO_yR^5$, —$SO_yCF_3$, —($C_1$–$C_6$ alkylene)-$SO_yCF_3$, —$CO_2R^5$, —($C_0$–$C_6$ alkylene)-$CO_2R^5$ or $OCF_3$, said phenyl being optionally additionally substituted by halo, —CN, —$COR^5$, —$CONR^5R^5$, —$SO_2NR^5R^5$, —$NR^5SO_2R^5$, —$OR^5$, —$NR^5R^5$, —($C_1$–$C_6$ alkylene)-$NR^5R^5$, $C_1$–$C_6$ alkyl, halo($C_1$–$C_6$)alkyl or $C_3$–$C_7$ cycloalkyl.

Preferably, $R^1$ is phenyl substituted by —$SO_yR^5$, ($C_1$–$C_6$ alkylene)-$SO_yR^5$, —$CO_2R^5$, or —($C_0$–$C_6$ alkylene)-$CO_2R^5$, said phenyl being optionally additionally substituted by halo, —CN, —$COR^5$, —$CONR^5R^5$, —$SO_2NR^5R^5$, —$NR^5SO_2R^5$, —$OR^5$, —$NR^5R^5$, —($C_1$–$C_6$ alkylene)-$NR^5R^5$, $C_1$–$C_6$ alkyl, halo($C_1$–$C_6$)alkyl or $C_3$–$C_7$ cycloalkyl.

Preferably, $R^1$ is phenyl substituted by —$SO_yR^5$, ($C_1$–$C_6$ alkylene)-$SO_yR^5$, —$CO_2R^5$, or —$C_0$–$C_6$ alkylene)-$CO_2R^5$.

Preferably, $R^1$ is phenyl substituted by —$SO_y(C_1$–$C_2$ alkyl) or —($C_1$–$C_2$ alkylene)-$SO_y(C_1$–$C_2$ alkyl).

Preferably, $R^2$ is H, $C_1$–$C_6$ alkyl, $C_3$–$C_6$ alkenyl, phenyl, benzyl or $R^9$, said phenyl, benzyl or $C_1$–$C_6$ alkyl being optionally substituted by halo, —$OR^5$, —$OR^{10}$, —CN, —$CO_2R^7$, —$OCONR^5R^5$, —$CONR^5R^5$, —C(=$NR^5$)

$NR^5OR^5$, $-CONR^5NR^5R^5$, $-NR^6R^6$, $-NR^5R^{10}$, $-NR^5COR^5$, $-NR^5COR^8$, $-NR^5COR^{10}$, $-NR^5CO_2R^5$, $-NR^5CONR^5R^5$, $-SO_2NR^5R^5$, $-NR^5SO_2R^5$, $R^8$ or $R^9$.

Preferably, $R^2$ is H $C_1$–$C_6$ alkyl, phenyl or benzyl, said $C_1$–$C_6$ alkyl being optionally substituted by halo, $-OR^5$, $-OR^{10}$ or $-NH_2$.

Preferably, $R^2$ is H or $C_1$–$C_3$ alkyl optionally substituted by $-OH$ or $-NH_2$.

Preferably, $R^2$ is H.

Preferably, $R^3$ is H, $C_1$–$C_6$ alkyl or $C_3$–$C_7$ cycloalkyl, said $C_1$–$C_6$ alkyl being optionally substituted by halo, $-CN$, $-OR^5$, $-CO_2R^5$, $-CONR^5R^5$, $-OCONR^5R^5$, $-NR^5CO_2R^5$, $-NR^6R^6$, $-NR^5COR^5$, $-SO_2NR^5R^5$, $-NR^5CONR^5R^5$, $-NR^5SO_2R^5$, $R^8$ or $R^9$.

Preferably, $R^3$ is H, $C_1$–$C_6$ alkyl or $C_3$–$C_7$ cycloalkyl.

Preferably, $R^3$ is H, $C_1$–$C_3$ alkyl or cyclopropyl.

Preferably, $R^3$ is methyl, ethyl or cyclopropyl.

Preferably, $R^4$ is phenyl optionally substituted by $R^8$, halo, $-CN$, $C_1$–$C_6$ alkyl, $C_1$–$C_6$ haloalkyl, $C_3$–$C_7$ cycloalkyl or $C_1$–$C_6$ alkoxy.

Preferably, $R^4$ is phenyl substituted by $R^8$, halo, $-CN$, $C_1$–$C_6$ alkyl, or $C_1$–$C_6$ alkoxy.

Preferably, $R^4$ is phenyl substituted by halo, $-CN$, $C_1$–$C_6$ alkyl, or $C_1$–$C_6$ alkoxy.

Preferably, $R^4$ is phenyl substituted by $-CN$.

Preferably, $R^4$ is 3,5-dicyanophenyl.

Preferably, $R^5$ is H or $C_1$–$C_4$ alkyl.

Preferably, $R^5$ is $C_1$–$C_2$ alkyl.

Preferably, $R^8$ is pyrrolyl, imidazolyl, pyrazolyl, 1,2,3-triazolyl, 1,2,4-triazolyl, tetrazolyl, oxazolyl, isoxazolyl, thiazolyl, isothiazolyl, 1,2,4-oxadiazolyl, 1,3,4-oxadiazolyl, furanyl, thienyl, pyridinyl, pyridazinyl, pyrimidinyl or pyrazinyl, each being optionally substituted by halo, $-CN$, $-COR^5$, $-CONR^5R^5$, $-SO_2NR^5R^5$, $-NR^5SO_2R^5$, $-OR^5$, $-NR^5R^5$, $-(C_1$–$C_6$ alkylene)-$NR^5R^5$, $C_1$–$C_6$ alkyl, fluoro($C_1$–$C_6$)alkyl or $C_3$–$C_7$ cycloalkyl.

Preferably, $R^8$ is imidazolyl, pyrazolyl, 1,2,4-triazolyl, 1,2,4-oxadiazolyl, 1,3,4-oxadiazolyl, pyridinyl, pyrazinyl or pyrimidinyl, each being optionally substituted by halo, $-CN$, $-COR^5$, $-CONR^5R^5$, $-SO_2NR^5R^5$, $-NR^5SO_2R^5$, $-OR^5$, $-NR^5R^5$, $-(C_1$–$C_6$ alkylene)-$NR^5R^5$, $C_1$–$C_6$ alkyl, fluoro($C_1$–$C_6$)alkyl or $C_3$–$C_7$ cycloalkyl.

Preferably, $R^8$ is imidazolyl, pyrazolyl, 1,2,4-triazolyl, 1,2,4-oxadiazolyl, 1,3,4-oxadiazolyl, pyridinyl, pyrazinyl or pyrimidinyl, each being optionally substituted by $-OR^5$, $-NR^5R^5$ or $C_1$–$C_6$ alkyl.

Preferably, $R^8$ is imidazolyl, pyrazolyl, 1,2,4-triazolyl, 1,2,4-oxadiazolyl, 1,3,4-oxadiazolyl, pyridinyl, pyrazinyl or pyrimidinyl, each being optionally substituted by $-OH$, $-NH_2$ or methyl.

Preferably, $R^9$ is azetidinyl, tetrahydropyrrolyl, piperidinyl, azepinyl, oxetanyl, tetrahydrofuranyl, tetrahydropyranyl, oxepinyl, morpholinyl, piperazinyl or diazepinyl, each being optionally substituted by oxo, $C_1$–$C_6$ alkyl, $C_3$–$C_7$ cycloalkyl, $-SO_2R^5$, $-CONR^5R^5$, $-COOR^5$, $-CO-(C_1$–$C_6$ alkylene)-$OR^5$ or $-COR^5$ and optionally substituted on a carbon atom which is not adjacent to a heteroatom by halo, $-OR^5$, $-NR^5R^5$, $-NR^5COR^5$, $-NR^5COOR^5$, $-NR^5CONR^5R^5$, $-NR^5SO_2R^5$ or $-CN$.

Preferably, $R^9$ is azetidinyl, piperidinyl, tetrahydrofuranyl, piperazinyl or morpholinyl, each being optionally substituted by oxo, $C_1$–$C_6$ alkyl, $C_3$–$C_7$ cycloalkyl, $-SO_2R^5$, $-CONR^5R^5$, $-COOR^5$, $-CO-(C_1$–$C_6$ alkylene)-$OR^5$ or $-COR^5$ and optionally substituted on a carbon atom which is not adjacent to a heteroatom by halo, $-OR^5$, $-NR^5R^5$, $-NR^5COR^5$, $-NR^5COOR^5$, $-NR^5CONR^5R^5$, $-NR^5SO_2R^5$ or $-CN$.

Preferably, $R^9$ is azetidinyl, piperidinyl, tetrahydrofuranyl, piperazinyl or morpholinyl, each being optionally substituted by $C_1$–$C_6$ alkyl, $-SO_2R^5$, $-CONR^5R^5$, $-COOR^5$, $-CO-(C_1$–$C_6$ alkylene)-$OR^5$ or $-COR^5$ and optionally substituted on a carbon atom which is not adjacent to a heteroatom by $-OR^5$ or $-NR^5COR^5$.

Preferably, $R^9$ is azetidinyl, piperidinyl, tetrahydrofuranyl, piperazinyl or morphoninyl, each being optionally substituted by $-CH_3$, $-SO_2CH_3$, $-CONH_2$, $-COOCH_3$, $-COCH_2OCH_3$ or $-COCH_3$ and optionally substituted on a carbon atom which is not adjacent to a heteroatom by $-OCH_3$ or $-NHCOCH_3$.

Preferably, $R^{10}$ is $C_1$–$C_4$ alkyl substituted by $R^8$, $R^9$, $-OR^5$, $-CONR^5R^5$, $-NR^5COR^5$ or $-NR^5R^5$.

Preferably, $R^{10}$ is $C_1$–$C_4$ alkyl substituted by $R^9$, $-OR^5$, $-NR^5COR^5$ or $-NR^5R^5$.

Preferably, $R^{10}$ is $C_1$–$C_2$ alkyl substituted by tetrahydrofuranyl, $-OCH_3$, $-NHCOCH_3$ or $-NH_2$.

Preferably, $R^{11}$ is phenyl substituted by halo, $-CN$, $-COR^5$, $-CONR^5R^5$, $-SO_2NR^5R^5$, $-NR^5SO_2R^5$, $-OR^5$, $-NR^5R^5$, $-(C_1$–$C_6$ alkylene)-$NR^5R^5$, $C_1$–$C_6$ alkyl, halo($C_1$–$C_6$)alkyl or $C_3$–$C_7$ cycloalkyl.

Preferably, $R^{11}$ is phenyl substituted by halo, $-CN$, $-CONR^5R^5$, $-SO_2NR^5R^5$ or $-OR^5$.

Preferably, $R^{11}$ is phenyl substituted by $-OR^5$.

Preferably, $R^{11}$ is phenyl substituted by $C_1$–$C_2$ alkoxy.

Preferred compounds according to the invention include all combinations of the preferred definitions for individual substituents given above.

Preferred compounds according to the invention include those of formula (Ia),

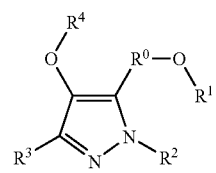

(Ia)

and pharmaceutically acceptable salts, solvates or derivatives thereof, wherein:

$R^0$ is $C_1$–$C_3$ alkylene;

$R^1$ is phenyl substituted by $-SO_yR^5$, $(C_1$–$C_6$ alkylene)-$SO_yR^5$, $-CO_2R^5$, or $-(C_0$–$C_6$ alkylene)-$CO_2R^5$, said phenyl being optionally additionally substituted by halo, $-CN$, $-COR^5$, $-CONR^5R^5$, $-SO_2NR^5R^5$, $-NR^5SO_2R^5$, $-OR^5$, $-NR^5R^5$, $-(C_1$–$C_6$ alkylene)-$NR^5R^5$, $C_1$–$C_6$ alkyl, halo($C_1$–$C_6$)alkyl or $C_3$–$C_7$ cycloalkyl;

$R^2$ is H or $C_1$–$C_3$ alkyl optionally substituted by $-OH$ or $-NH_2$;

$R^3$ is H, $C_1$–$C_3$ alkyl or cyclopropyl;

$R^4$ is phenyl substituted by halo, $-CN$, $C_1$–$C_6$ alkyl, or $C_1$–$C_6$ alkoxy;

$R^5$ is H or $C_1$–$C_4$ alkyl; and y is 0, 1 or 2.

Within the compounds of formula (Ia), preferably $R^1$ is phenyl substituted by $-SO_yR^5$, $(C_1$–$C_6$ alkylene)-$SO_yR^5$, $-CO_2R^5$, or $-C_0$–$C_6$ alkylene)-$CO_2R^5$ Preferred compounds of the invention are:
5-[(3-Ethyl-5-{2-[4-(methylsulfanyl)phenoxy]ethyl}-1H-pyrazol-4-yl)oxy]isophthalonitrile;
5-[(3-Ethyl-5-{2-[4-(methylsulfonyl)phenoxy]ethyl}-1H-pyrazol-4-yl)oxy]isophthalonitrile;
and pharmaceutically acceptable salts, solvates or derivatives thereof.

The compounds of the invention may have advantages over those of the prior art with regard to a number of useful properties or combination thereof, such as potency, duration of action, pharmacokinetics, spectrum of activity, side effect profile, solubility, chemical stability, and so on.

The compounds of the invention may be prepared by any method known in the art for the preparation of compounds of analogous structure. The compounds of the invention can be prepared by the procedures described in the methods below, or by the specific methods described in the Examples, or by similar methods to either. The invention also encompasses any one or more of these processes for preparing the compounds of the invention, in addition to any novel intermediates used therein.

In the following methods $R^0$ to $R^4$ are as previously defined for a compound of formula (I), unless otherwise stated, and Lg, $Lg^1$ and $Lg^2$ are leaving groups, such as halogen (e.g. Cl) or sulfonate ester (e.g. trifluoromethanesulfonate or methanesulfonate).

Compounds of formula (I) may be prepared according to Scheme 1.

According to Scheme 1, compounds of formula (I) may be prepared by the reaction of a compound of formula (V) with an alcohol of formula (IV) under conventional conditions. Conveniently, the reaction is effected in the presence of a base, such as a trialkylamine (e.g. triethylamine), a carbonate (e.g. potassium or caesium carbonate) or hydroxide (e.g. sodium hydroxide); a solvent, such as a haloalkane (e.g. dichloromethane); and at ambient to elevated temperature, such as under reflux.

Compounds of formula (V) may be prepared from compounds of formula (III) by derivatising the hydroxy group therein to provide a leaving group ($Lg^2$). Conveniently, $Lg^2$ is a reactive ester group, such as a sulphonic ester group, (e.g. methanesulphonate). Conveniently, the reaction is effected in the presence of a derivatising agent, such as an alkylsulphonyl halide, (e.g. methanesulphonyl chloride); a base, such as a trialkylamine base (e.g. triethylamine); a solvent such, such as a halogenated alkane (e.g. dichloromethane); and at ambient to elevated temperature, such as ambient temperature.

Compounds of formula (III) may be prepared by the reaction of a compound of formula (VII) with a hydrazine of formula (VI), or a salt or hydrate thereof. Conveniently, the reaction is effected in a solvent, such as a protic solvent (e.g. acetic acid); at ambient to elevated temperature, such as

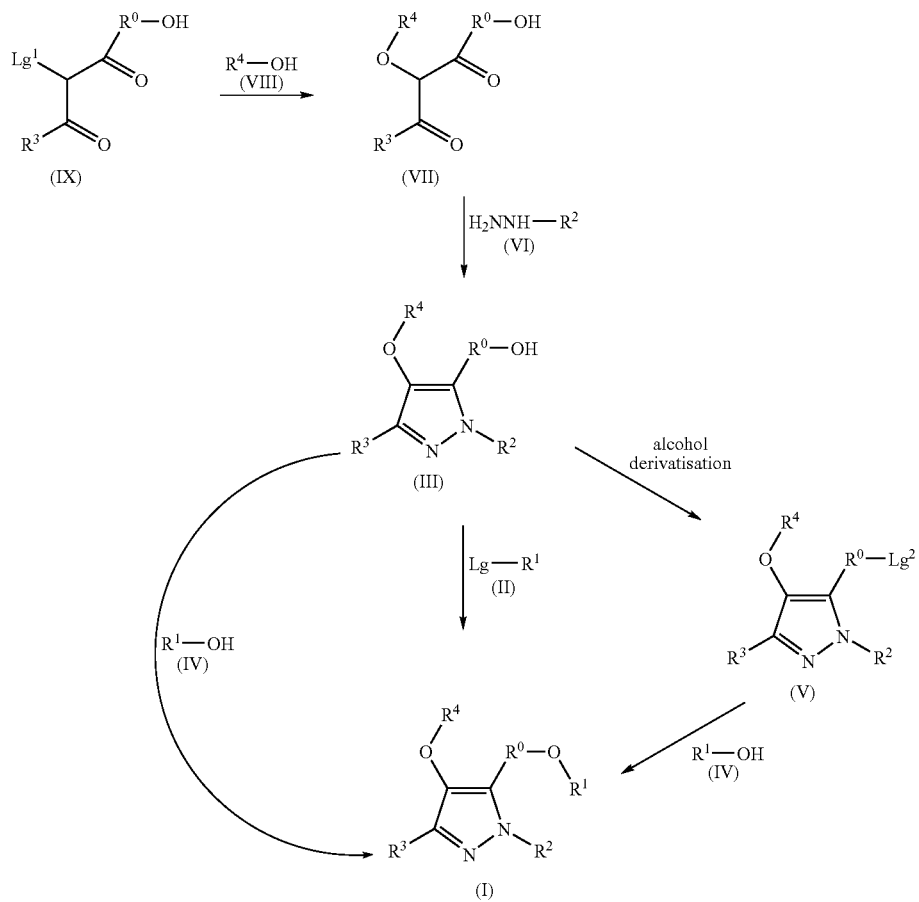

Scheme 1 ambient temperature; and optionally in the presence of an acid (e.g. acetic acid) or a base, such as a tertiary amine (e.g. triethylamine).

Compounds of formula (VII) may be prepared by the reaction of a compound of formula (IX) with an alcohol of formula (VIII). Conveniently, the reaction is effected in the presence of a solvent, such as a polar solvent (e.g. acetone); a base, such as an inorganic base, preferably a metal carbonate (e.g. potassium or caesium carbonate); optionally, a nucleophilic catalyst, such as sodium iodide or tetrabutylammonium iodide; and at ambient to elevated temperature, such as elevated temperature (e.g. under reflux).

Ketoesters of formula (IX) are either commercially available, known in the literature, or may be prepared by conventional methods (e.g., where $Lg^1$ is Cl, by the chlorination of corresponding ketoesters, for instance using sulphonyl chloride).

According to Scheme 1, compounds of formula (I) may also be prepared by the reaction of an alcohol of formula (III) with a compound of formula (II) under conventional conditions. Conveniently, the reaction is effected in the presence of a base, such as an inorganic base, preferably a metal carbonate (e.g. potassium carbonate); optionally a solvent, such as a polar aprotic solvent (e.g. N,N-dimethylacetamide); optionally a catalyst, such as a copper(I) catalyst; and at ambient to elevated temperature, such as elevated temperature (e.g. under reflux).

According to Scheme 1, compounds of formula (I) may also be prepared by the reaction of an alcohol of formula (III) with an alcohol of formula (IV) under dehydrating conditions, such as afforded by the Mitsunobu reaction. Conveniently, the reaction is effected in the presence of an azodicarboxylate, such as diisopropylazodicarboxylate; triphenylphosphine; a solvent, such as an ether (e.g. tetrahydrofuran); and at reduced to ambient temperature, such 0° C. to ambient temperature.

Compounds of formula (I) in which $R^3$ is halo can be prepared from a compound of formula (X)

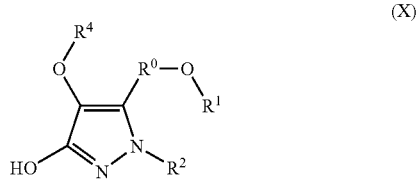

(X)

under conventional conditions. Conveniently, the reaction is effected by an inorganic acid halide, such as an inorganic acid chloride (e.g. $POCl_3$); optionally in the presence of a solvent, such as a polar aprotic solvent (e.g. N,N-dimethylformamide); and at reduced to ambient temperature, such as ambient temperature.

Compounds of formula (X) may be prepared using the routes described above, mutatis mutandis.

It will be appreciated by those skilled in the art that, in many cases, it may be necessary or desirable to protect one or more sensitive functional groups, for example hydroxy groups, in the preparation of compounds of formula (I), as for example set out in Scheme 1. In particular, it may be necessary or desirable to protect the —$R^0$—OH group of compounds of formulae (IX), (VII) and (III), and to deprotect the group prior to further transformation of a compound of formula (III). Likewise, when $R^2$ is H, it may be necessary or desirable to protect the pyrazole NH group of compounds of formulae (III), (V) and (I) and to deprotect the group to provide a compound of formula (I). Examples of suitable protecting groups will be apparent to the skilled person. See, for instance, 'Protecting groups in Organic Synthesis (Second Edition)' by Theodora W. Green and Peter G. M. Wuts, 1991, John Wiley and Sons (in particular pages 10–118, relating to protection for the hydroxyl group, and pages 309 to 405, relating to protection for the amino group, both of which describe methods for protection and subsequent deprotection), incorporated herein by reference.

It will be appreciated by those skilled in the art that compounds of formula (I) containing an —OH, —NH— or —$NH_2$ group may be prepared by deprotection of the corresponding compound bearing an —$OP^1$, —$NP^1$— or —$NHP^1$ group, respectively, wherein the group $P^1$ is a suitable protecting group. Such compounds bearing an —$OP^1$, —$NP^1$— or —$NHP^1$ group may be prepared using the routes described above, mutatis mutandis.

It will be appreciated by those skilled in the art that, in many cases, compounds of formula (I) may be converted into other compounds of formula (I) by functional group transformations, including for example the following interconversions.

Compounds of formula (I) in which $R^1$ is phenyl substituted by $C_1$–$C_6$ alkylsulfinyl or $C_1$–$C_6$ alkylsulfonyl may be prepared by oxidation of the corresponding compound of formula (I) wherein $R^1$ is phenyl substituted by $C_1$–$C_6$ alkylsulfanyl. The skilled artisan will appreciate that, depending on the severity of the oxidatitive conditions employed, such alkylsulfinyls of formula (I) may be partially oxidised to corresponding alkylsulfinyls, or fully oxidised to corresponding alkylsulfonyls. For the preparation of $C_1$–$C_6$ alkylsulfinyl compounds the oxidation is, conveniently, effected in the presence of an oxidising agent, such as oxone; optionally in the presence of a moderator, such as wet alumina; a solvent, such as a haloalkane (e.g. dichloromethane); and carried out at ambient to elevated temperature, such as under reflux. For the preparation of $C_1$–$C_6$ alkylsulfonyl compounds the oxidation is, conveniently, effected in the presence of an oxidising agent, such as oxone; a solvent, such as an aqueous alcohol (e.g. aqueous methanol); and at reduced to ambient temperature (e.g. 0° C.).

Compounds of formula (I) in which $R^2$ is optionally substituted $C_1$–$C_6$ alkyl may be prepared from compounds of formula (I) in which $R^2$ is H by reaction with an alkylating agent. Suitable alkylating agents include bromoacetonitrile, ethyl 4-chloroacetoacetate, methyl bromoacetate and chloroethylamine hydrochloride. Conveniently, alkylation is effected in the presence of a suitable solvent, such as an alcohol (e.g. ethanol) or a polar aprotic solvent (e.g. N,N-dimethylformamide); a base, such as a metal hydride (e.g. sodium hydride) or metal alkoxide (e.g. sodium ethoxide); and at ambient to elevated temperature, such as under reflux.

Compounds of formula (I) in which $R^2$ or $R^3$ contains a hydroxy group may be prepared from the corresponding compound of formula (I) in which $R^2$ or $R^3$ contains an ester group by reduction. Conveniently, the reduction is effected by a metal hydride, such as lithium aluminium hydride; in a solvent, such as an ether (e.g. diethyl ether); and at reduced temperature, such as from −78° C. to 0° C.

Compounds of formula (I) in which $R^2$ or $R^3$ are substituted by a heterocycle of formula $R^8$ and $R^9$ may be prepared by standard heterocycle-forming reactions well known to the skilled man (see, for example, Advanced Organic Chemistry, 3rd Edition, by Gerry March or Comprehensive Heterocyclic Chemistry, A. R. Katritzky, C. W. Rees, E. F. V. Scriven, Volumes 1–11).

Compounds of formula (I) in which $R^3$ is —$CO_2H$ may be prepared by hydrolysis of a corresponding compound of formula (I) in which $R^3$ is —$CO_2R^5$. Conveniently, the reaction is effected in the presence of a solvent, such as an alcohol (e.g. aqueous ethanol), or an ether (e.g. aqueous 1,4-dioxan); and in the presence of a base, such as a metal hydroxide (e.g. sodium hydroxide). The skilled artisan will appreciate that such an acid may be converted into a primary amide by reaction with ammonia and a suitable coupling agent, such as a carbodiimide, e.g. dicyclohexylcarbodiimide, and that such a primary amide may then be converted into a nitrile by dehydration with a suitable dehydrating agent, such as phosphoryl chloride.

Compounds of formula (I) in which $R^3$ is $C_1$–$C_6$ alkyl may be converted into the compounds of formula (I) in which $R^3$ is $C_1$–$C_6$ alkyl substituted by halo (such as bromo), by halogenation, using a suitable halogenating agent. Conveniently the reaction is effected in the presence of a solvent, such as a haloalkane (e.g. dichloromethane) and at ambient temperature. Suitable halogenating agents include halogens (e.g. bromine) or N-halosuccinimides (e.g. N-bromsuccinimide).

Compounds of formulae (II), (IV) and (VI) and (VIII) are either commercially available, known in the literature or easily prepared by methods well known to those skilled in the art, such as those described in the Preparations hereinafter.

Compounds of formulae (III), (V) or (X) are key intermediates and form a further aspect of the invention.

The compounds of the invention can be administered alone, but will generally be administered in admixture with a suitable pharmaceutical excipient, diluent or carrier selected with regard to the intended route of administration and standard pharmaceutical practice.

For example, the compounds of the invention can be administered orally, buccally or sublingually in the form of tablets, capsules, multi-particulates, gels, films, ovules, elixirs, solutions or suspensions, which may contain flavouring or colouring agents, for immediate-, delayed-, modified-, sustained-, pulsed- or controlled-release applications. The compounds of the invention may also be administered as fast-dispersing or fast-dissolving dosage forms or in the form of a high energy dispersion or as coated particles. Suitable formulations of the compounds of the invention may be in coated or uncoated form, as desired.

Such solid pharmaceutical compositions, for example, tablets, may contain excipients such as microcrystalline cellulose, lactose, sodium citrate, calcium carbonate, dibasic calcium phosphate, glycine and starch (preferably corn, potato or tapioca starch), disintegrants such as sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

General Example

A formulation of the tablet could typically contain from 0.01 mg to 500 mg of active compound whilst tablet fill weights may range from 50 mg to 1000 mg. An example of a formulation for a 10 mg tablet is illustrated below:

| Ingredient | % w/w |
|---|---|
| Compound of the invention | 10.000* |
| Lactose | 64.125 |
| Starch | 21.375 |
| Croscarmellose sodium | 3.000 |
| Magnesium Stearate | 1.500 |

*Quantity adjusted in accordance with drug activity.

The tablets are manufactured by a standard process, for example, direct compression or a wet or dry granulation process. The tablet cores may be coated with appropriate overcoats.

Solid compositions of a similar type may also be employed as fillers in gelatin or HPMC capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

The compounds of the invention can also be administered parenterally, for example, intravenously, intra-arterially, intraperitoneally, intrathecally, intraventricularly, intraurethrally, intrasternally, intracranially, intramuscularly or subcutaneously, or they may be administered by infusion or needleless injection techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of the compounds of the invention will usually be from 0.01 to 30 mg/kg, preferably from 0.01 to 5 mg/kg (in single or divided doses).

Thus tablets or capsules of the compound of the invention may contain from 1 to 500 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention. The skilled person will appreciate that, in the treatment of certain conditions the compounds of the invention may be taken as a single dose as needed or desired.

The compounds of invention can also be administered intranasally or by inhalation and are conveniently delivered in the form of a dry powder inhaler or an aerosol spray presentation from a pressurised container, pump, spray, atomiser or nebuliser, with or without the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray, atomiser or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Alternatively, the compounds of the invention can be administered in the form of a suppository or pessary, or they may be applied topically in the form of a gel, hydrogel, lotion, solution, cream, ointment or dusting powder. The compounds of the invention may also be dermally or transdermally administered, for example, by the use of a skin patch. They may also be administered by the pulmonary or rectal routes.

They may also be administered by the ocular route. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyidodecanol, benzyl alcohol and water.

The compounds of the invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO91/11172, WO94/02518 and WO98/55148.

It is to be appreciated that all references herein to treatment include curative, palliative and prophylactic treatment.

Oral administration is preferred.

Included within the scope of the invention are embodiments comprising the co-administration of a compound of the invention with one or more additional therapeutic agents, and compositions containing a compound of the invention along with one or more additional therapeutic agents. Such a combination therapy is especially useful for the prevention and/or treatment of infection by HIV and related retroviruses which may evolve rapidly into strains resistant to any monotherapy. Alternatively, additional therapeutic agents may be desirable to treat diseases and conditions which result from or accompany the disease being treated with the compound of the invention. For example, in the treatment of an HIV or related retroviral infection, it may be desirable to additionally treat opportunistic infections, neoplasms and other conditions which occur as a result of the immunocompromised state of the patient being treated.

Preferred combinations of the invention include simultaneous or sequential treatment with a compound of the invention and one or more:
(a) reverse transcriptase inhibitors such as abacavir, adefovir, didanosine, lamivudine, stavudine, zalcitabine and zidovudine;
(b) non-nucleoside reverse transcriptase inhibitors such as capavirine, delavirdine, efavirenz, and nevirapine;
(c) HIV protease inhibitors such as indinivir, nelfinavir, ritonavir, and saquinavir;
(d) CCR5 antagonists such as TAK-779 or UK-427,857;
(e) CXCR4 antagonists such as AMD-3100;
(f) integrase inhibitors, such as L-870,810 or S-1360;
(g) inhibitors of viral fusion such as T-20;
(h) investigational drugs such as trizivir, KNI-272, amprenavir, GW-33908, FTC, PMPA, MKC-442, MSC-204, MSH-372, DMP450, PNU-140690, ABT-378, KNI-764, DPC-083, TMC-120 or TMC-125;
(i) antifungal agents, such as fluconazole, itraconazole or voriconazole; or
(j) antibacterial agents, such as azithromycin.

The activity of the compounds of the invention as reverse transcriptase inhibitors may be measured using the following assay.

Inhibition of HIV-1 Reverse Transcriptase Enzyme

Using purified recombinant HIV-1 reverse transcriptase (RT, EC, 2.7.7.49) obtained by expression in *Escherichia Coli*, a 96-well plate assay system is established for assaying a large number of samples using either the Poly(rA)-oligo (dT) Reverse Transcriptase [3H]-SPA enzyme assay system (Amersham NK9020) or the [3H]-flashplate enzyme assay system (NEN-SMP 103) and following the manufacturer's recommendations. The compounds are dissolved in 100% DMSO and diluted with the appropriate buffer to a 5% final DMSO concentration. The inhibitory activity is expressed in percent inhibition relative to DMSO control. The concentration at which compound inhibits reverse transcriptase by 50% is expressed as the $IC_{50}$ of the compound.

The compound of Examples 1 and 3, when tested according to the above procedure, had an $IC_{50}$ values of, respectively, 2 and 45 nanomolar.

Thus the invention provides:
(i) a compound of formula (I) or a pharmaceutically acceptable salt, solvate or derivative thereof;
(ii) a process for the preparation of a compound of formula (I) or a pharmaceutically acceptable salt, solvate or derivative thereof;
(iii) a pharmaceutical composition including a compound of formula (I) or a pharmaceutically acceptable salt, solvate or derivative thereof, together with a pharmaceutically acceptable excipient, diluent or carrier;
(iv) a compound of formula (I) or a pharmaceutically acceptable salt, solvate or composition thereof, for use as a medicament;
(v) a compound of formula (I) or a pharmaceutically acceptable salt, solvate or composition thereof, for use as a reverse transcriptase inhibitor or modulator;
(vi) a compound of formula (I) or a pharmaceutically acceptable salt, solvate or composition thereof, for use in the treatment of an HIV or genetically-related retroviral infection, or a resulting acquired immune deficiency syndrome (AIDS);

(vii) a use of the compound of formula (I) or of a pharmaceutically acceptable salt, solvate or composition thereof, for the manufacture of a medicament having reverse transcriptase inhibitory or modulating activity;

(viii) the use of a compound of formula (I) or of a pharmaceutically acceptable salt, solvate or composition thereof, for the manufacture of a medicament for the treatment of an HIV or genetically-related retroviral infection, or a resulting acquired immune deficiency syndrome (AIDS);

(ix) a method of treating an HIV or a genetically-related retroviral infection, or a resulting acquired immune deficiency syndrome (AIDS), comprising administering an effective amount of a compound of formula (I) or a pharmaceutically acceptable salt, solvate or composition thereof; and (xi) certain novel intermediates disclosed herein.

The following Examples illustrate the preparation of the compounds of formula (I). The synthesis of certain intermediates used therein are described in the Preparations section that follows the Examples.

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The following abbreviations have been used: HRMS, high resolution mass spectrometry; hplc, high performance liquid chromatography; nOe, nuclear Overhauser effect; m.p., melting point; CDCl$_3$, deuterochloroform; D$_6$-DMSO, deuterodimethylsulphoxide; CD$_3$OD, deuteromethanol. Where thin layer chromatography (TLC) has been used it refers to silica gel TLC using silica gel 60 F$_{254}$ plates, R$_f$ is the distance travelled by a compound divided by the distance travelled by the solvent front on a TLC plate.

EXAMPLE 1

5-[(3-Ethyl-5-{2-[4-(methylsulfanyl)phenoxy]ethyl}-1H-pyrazol-4-yl)oxy]isophthalonitrile

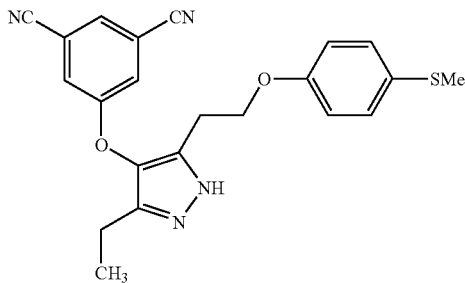

To a stirred solution of the alcohol from Preparation 10 (268 mg, 0.95 mmol) in tetrahydrofuran (8 ml) at 0° C. was added 4-(methylmercatpto)phenol (200 mg, 1.43 mmol), triphenylphosphine (374 mg, 1.43 mmol) and diisopropylazodicarboxylate (275 µl, 1.43 mmol). The reaction was allowed to warm to room temperature and was stirred for 18 hours. The mixture was concentrated under reduced pressure and purified by flash chromatography on silica gel eluting with dichloromethane:methanol (95:5, by volume). Column chromatography was repeated eluting with ethyl acetate and then repeated eluting with ethyl acetate:toluene (25:75, by volume) and finally repeated eluting with ethyl acetate:toluene (15:85, by volume) to give the title compound as a colourless oil (153 mg).

$^1$H NMR (400 MHz, CDCl$_3$): δ=1.20 (t, 3H), 2.44 (s, 3H), 2.50 (q, 2H), 2.97 (t, 2H), 4.15 (t, 2H), 6.71 (d, 2H), 7.20 (d, 2H), 7.38 (s, 2H), 7.53 (s, 1H). LRMS (atmospheric chemical ionisation): m/z [MH$^+$] 405.

EXAMPLE 2

5-[(3-Ethyl-5-{2-[4-(methylsulfinyl)phenoxy]ethyl}-1H-pyrazol-4-yl)oxy]isophthalonitrile

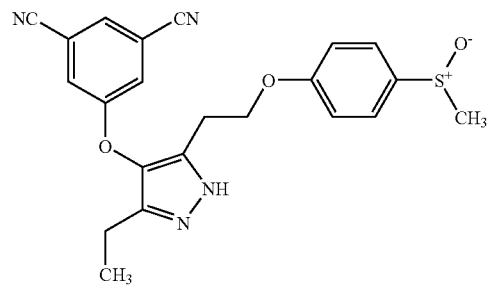

Wet alumina was prepared by adding water (1 ml) to Brockman grade I alumina (5 g). A sample of this material (160 mg) was added to a stirred solution of the sulfide from Example 1 (106 mg, 0.16 mmol) in dichloromethane (1 ml), followed by oxone (98 mg, 0.16 mmol). The reaction mixture was heated at reflux for 45 minutes, before being filtered. The solids were washed with dichloromethane (10 ml) and the combined organics were concentrated under reduced pressure. The crude product mixture was purified by flash chromatography on silica gel eluting with dichloromethane:methanol (100:0, 98:2 and 96:4, by volume) to give the title compound as a colourless oil (25 mg).

$^1$H NMR (400 MHz, CDCl$_3$): δ=1.19 (t, 3H), 2.50 (q, 2H), 2.71 (s, 3H), 2.99 (t, 2H), 4.23 (t, 2H), 6.92 (d, 2H), 7.39 (s, 2H), 7.55 (s, 1H), 7.56 (d, 2H). LRMS (atmospheric pressure chemical ionisation): m/z [MH$^+$] 421 Accurate Mass: Found: 421.1323 [MH$^+$]; C$_{22}$H$_{21}$N$_4$O$_3$S requires 421.1329 [MH$^+$].

EXAMPLE 3

5-[(3-Ethyl-5-{2-[4-(methylsulfonyl)phenoxy]ethyl}-1H-pyrazol-4-yl)oxy]isophthalonitrile

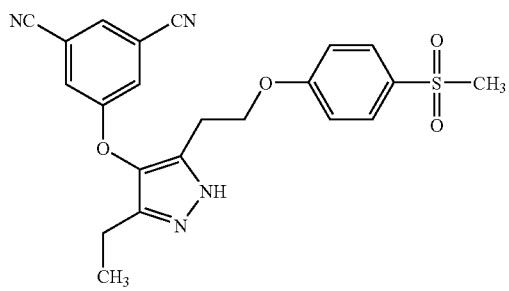

To a stirred solution of the sulfide from Example 1 (90 mg, 0.22 mmol) in methanol (2 ml) at 0° C. was added a solution of oxone (205 mg, 0.33 mmol) in water (2 ml). The viscous suspension was further diluted with methanol (2 ml). After 4 hours the reaction mixture was concentrated under reduced pressure and the residue was partitioned between dichloromethane (20 ml) and water (20 ml). The organic layer was dried over magnesium sulfate, filtered and concentrated under reduced pressure. The crude product mixture was purified by flash chromatography on silica gel eluting with pentane:ethyl acetate (50:50, by volume) to give the title compound (70 mg) as a white powder, m.p. 88–90° C.

$^1$H NMR (400 MHz, CDCl$_3$): δ=1.20 (t, 3H), 2.51 (q, 2H), 3.00 (t, 2H), 3.03 (s, 3H), 4.27 (t, 2H), 6.92 (d, 2H), 7.39 (s, 2H), 7.56 (s, 1H), 7.84 (d, 2H). LRMS (atmospheric pressure chemical ionisation): m/z [MH$^+$] 437 Microanalysis: Found: C, 60.17; H, 4.60; N, 12.73. C$_{22}$H$_{20}$N$_4$O$_4$S requires C, 60.54; H, 4.62; N, 12.84%.

EXAMPLE 4

5-[(3-Ethyl-5-{2-[3-(methylsulfany)phenoxy]ethyl}-1H-pyrazol-4-yl)oxy]isophthalonitrile

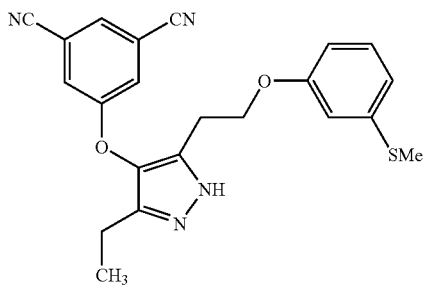

To a stirred solution of the alcohol from Preparation 10 (395 mg, 1.40 mmol) in tetrahydrofuran (14 ml) at 0° C. was added 3-(methylmercatpto)phenol (196 mg, 1.40 mmol), triphenylphosphine (367 mg, 1.40 mmol) and diethylazodicarboxylate (276 μl, 1.60 mmol). The reaction was allowed to warm to room temperature and was stirred for 18 hours. The mixture was concentrated under reduced pressure and purified by flash chromatography on silica gel eluting with pentane:ethyl acetate (9:1, 5:1 and 3:1 by volume). Column chromatography was repeated eluting with dichloromethane:acetonitrile (100:0, 99:1, 98:2 and 97:3 by volume) to give the title compound as a colourless oil (207 mg, approximately 60% pure w/w) which was contaminated with triphenylphosphine oxide and the reduced diethylazodicarboxylate.

$^1$H NMR (400 MHz, CDCl$_3$): δ=1.16 (t, 3H), 2.45 (s, 3H), 2.48 (q, 2H), 2.96 (t, 2H), 4.16 (t, 2H), 6.53 (d, 1H), 6.62 (s, 1H), 6.81 (s, 1H), 7.13 (t, 1H), 7.35 (s, 2H). 7.53 (s, 1H). LRMS (atmospheric chemical ionisation): m/z [MH$^+$] 405.

EXAMPLE 5

5-[(3-Ethyl-5-{2-[3-(methylsulfinyl)phenoxy]ethyl}-1H-pyrazol-4-yl)oxy]isophthalonitrile

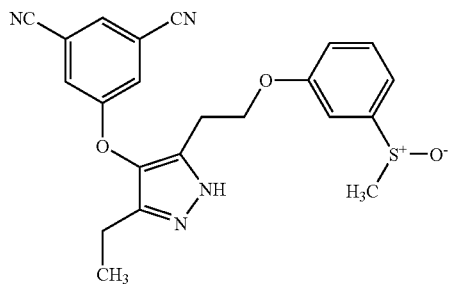

Wet alumina was prepared by adding water (1 ml) to Brockman grade I alumina (5 g). A sample of this material (320 mg) was added to a stirred solution of the sulfide from Example 4 (217 mg, 0.32 mmol) in dichloromethane (2 ml), followed by oxone (196 mg, 0.32 mmol). The reaction mixture was heated at reflux for 45 minutes, before being filtered. The solids were washed with dichloromethane (10 ml) and the combined organics were concentrated under reduced pressure. The crude product mixture was purified by flash chromatography on silica gel eluting with dichloromethane:methanol (100:0, 98:2 and 96:4, by volume) to give the title compound as a colourless oil (69 mg).

$^1$H NMR (400 MHz, CDCl$_3$): δ=1.19 (t, 3H), 2.12 (q, 2H), 2.73 (s, 3H), 2.99 (t, 2H), 4.27 (t, 2H), 6.88 (d, 1H), 7.10 (d, 1H), 7.20 (m, 1H), 7.37 (t, 1H), 7.39 (s, 2H), 7.54 (s, 1H). LRMS (atmospheric pressure chemical ionisation): m/z [MH$^+$] 421 Accurate Mass: Found: 421.1330 [MH$^+$]; C$_{22}$H$_{21}$N$_4$O$_3$S requires 421.1329 [MH$^+$].

EXAMPLE 6

5-[(3-Ethyl-5-{2-[3-(methylsulfonyl)phenoxy]ethyl}-1H-pyrazol-4-yl)oxy]isophthalonitrile

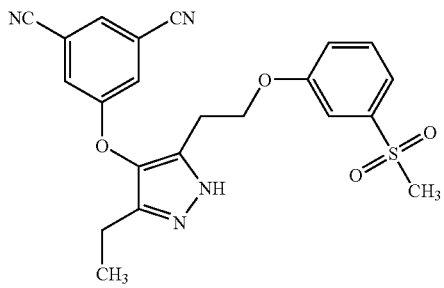

To a stirred solution of the sulfoxide from Example 5 (34 mg, 0.08 mmol) in methanol (1 ml) was added a solution of oxone (49 mg, 0.08 mmol) in water (1 ml). After 2 hours the reaction mixture was concentrated under reduced pressure and the residue was partitioned between dichloromethane (5 ml) and water (5 ml). The organic layer was dried over magnesium sulfate, filtered and concentrated under reduced pressure. The crude product mixture was purified by flash chromatography on silica gel eluting with dichloromethane:methanol (100:0, 99:1 then 98:2, by volume) to give the title compound as a colourless oil (12 mg).

$^1$H NMR (400 MHz, CDCl$_3$): δ=1.21 (t, 3H), 2.52 (q, 2H), 3.01 (t, 2H), 3.06 (s, 3H), 4.27 (t, 2H), 7.08 (d, 1H), 7.34 (t, 1H), 7.41 (s, 2H), 7.46 (t, 1H), 7.53 (m, 1H), 7.57 (s, 1H). LRMS (atmospheric pressure chemical ionisation): m/z [MH$^+$] 437 Accurate Mass: Found: 437.1279 [MH$^+$]; C$_{22}$H$_{21}$N$_4$O$_3$S requires 421.1278 [MH$^+$].

Preparation 1

1,3-Dibromo-5-methoxybenzene

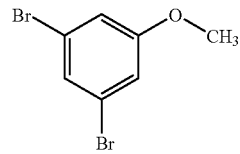

Sodium methoxide (8.80 ml of a 4.5M solution in methanol, 39.6 mmol) was added dropwise to a stirred solution of 3,5-dibromofluorobenzene (5.00 g, 19.0 mmol) in N,N-dimethylformamide (95 ml) at 0° C. under nitrogen. The reaction was allowed to warm to room temperature, stirred for 1 hour and then concentrated under reduced pressure. The residue was dissolved in ether (500 ml) and the resulting solution was washed with water (3×300 ml) and brine (300 ml), dried over magnesium sulphate, filtered and concentrated under reduced pressure to provide the title compound (5.13 g) as a white solid.

$^1$H-NMR (300 MHz, CDCl$_3$): δ=3.79 (s, 3H), 7.00 (s, 2H), 7.26 (s, 1H). LRMS (thermospray): m/z [MH$^+$] 266. Microanalysis: Found: C, 31.56; H, 2.29. C$_7$H$_6$OBr$_2$ requires C, 31.62; H, 2.27%.

Preparation 2

3,5-Dicyanomethoxybenzene

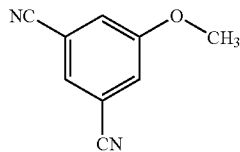

Tris(dibenzylideneacetone)dipalladium(0) (6.53 g, 7.15 mmol) was added in one portion to a stirred solution of the bromide of Preparation 1 (38.0 g, 143 mmol), 1,1'-bis(diphenylphosphino)ferrocene (9.3 g, 16.8 mmol) and zinc cyanide (20.0 g, 172 mmol) in N,N-dimethylformamide (300 ml) at room temperature under nitrogen. The reaction was heated at 100° C. for 14 hours and cooled to room temperature. Water (1500 ml) was added and the mixture was extracted with ethyl acetate (3×500 ml). The combined organics were filtered and the filtrate was washed with water (500 ml), dried over magnesium sulphate, filtered and concentrated under reduced pressure. The resulting solid was triturated with toluene (1000 ml) to provide the title compound (18.0 g) as a tan solid.

$^1$H-NMR (300 MHz, CDCl$_3$): δ=3.83 (3H, s), 7.31 (2H, s), 7.48 (1H, s).

Preparation 3

3,5-Dicyanohydroxybenzene

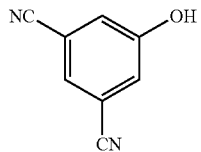

The nitrile of Preparation 2 (9.60 g, 60.7 mmol) was added portionwise to a stirred suspension of aluminium trichloride (32.4 g, 243 mmol) in dichloromethane (250 ml) at 0° C. under nitrogen. The suspension was heated to 45° C. and stirred for 6 days. The reaction was cooled to room temperature and cautiously poured onto ice (450 ml). Concentrated hydrochloric acid (450 ml) was added dropwise and the resulting suspension was stirred for 10 minutes at room temperature. The resulting solid was collected by filtration, washed with water and dried over phosphorus pentoxide to provide the title compound (7.83 g) as a tan solid containing approximately 10% starting material by $^1$H-NMR and microanalysis.

$^1$H-NMR (400 MHz, CDCl$_3$): δ=7.36 (m, 2H), 7.56 (m, 1H).

Preparation 4

3-Oxopentanoic acid

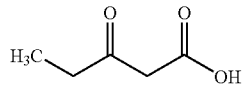

Sodium hydroxide (54 g, 1.35 mol) was added portionwise to a solution of 3-oxo-pentanoic acid methyl ester (80 g, 0.62 mol) in tetrahydrofuran (300 ml) and water (300 ml) at 0° C. The reaction was allowed to warm to room temperature and was stirred for 18 hours. The reaction mixture was washed with diethylether (500 ml) and the aqueous phase was acidified to pH1 at 0° C. with concentrated hydrochloric acid (140 ml). The aqueous phase was extracted with dichloromethane (2×300 ml) and the combined organic extracts dried over magnesium sulphate and concentrated under reduced pressure to provide the title compound (44 g) as a white solid.

$^1$H NMR (400 MHz, CDCl$_3$): δ=1.12 (t, 3H), 2.59 (q, 2H), 3.49 (s, 2H).

Preparation 5

3-(Benzyloxy)propanoic acid

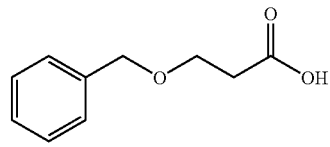

Sodium metal (249 mg, 10.8 mmol) was added to benzyl alcohol (30 g, 278 mmol) at room temperature under nitrogen and the reaction was stirred for 30 minutes. Methyl acrylate (25.9 ml, 259 mmol) was then added dropwise and the reaction was stirred at room temperature for 18 h. After quenching with saturated aqueous ammonium chloride solution (200 ml) the mixture was extracted with ethyl acetate (2×300 ml) and the combined organic extracts were washed with brine (100 ml), dried over magnesium sulphate and concentrated under reduced pressure. The residual oil was dissolved in ethanol (300 ml) and 1M aqueous sodium hydroxide solution (300 ml) was added dropwise. After 3 hours the ethanol was removed under reduced pressure and the aqueous residue was washed with dichloromethane (200 ml). The aqueous phase was then acidified with 2N aqueous hydrochloric acid (150 ml), extracted with dichloromethane (2×250 ml) and the combined organic extracts were dried over magnesium sulphate and concentrated under reduced pressure. The residual oil was dissolved in 10% aqueous potassium carbonate solution (300 ml), washed with diethylether (300 ml) and the aqueous phase was acidified to pH1 using concentrated hydrochloric acid. The mixture was then extracted with dichloromethane (2×300 ml) and the combined organic extracts were dried over magnesium sulphate and concentrated under reduced pressure to provide the title compound (44.4 g) as a colourless oil.

¹H NMR (300 MHz, CDCl₃): δ=2.67 (t, 2H), 3.89 (t, 2H), 4.58 (s, 2H), 7.18 (m, 5H).

Preparation 6

(4Z)-1-(Benzyloxy)-5-hydroxy-4-hepten-3-one

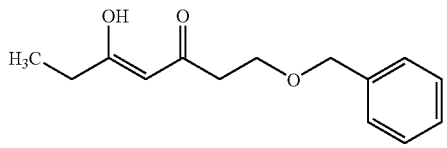

A suspension of magnesium turnings (1.74 g, 71.6 mmol) in methanol (85 ml) was heated at reflux under nitrogen for 1.5 hours, cooled to room temperature and the β-keto acid from Preparation 4 (16.6 g, 143 mmol) was added. The reaction was stirred for 1.5 hours and the solvent was removed under reduced pressure to give the magnesium salt of the acid as a white solid. Meanwhile, the acid from Preparation 5 (12.9 g, 71.6 mmol) was dissolved in N,N'-dimethylformamide (150 ml) and carbonyldiimidazole (12.8 g, 78.8 mmol) was added portionwise under nitrogen at room temperature. This was stirred for 1 hour and then the magnesium salt from above was added as a solution in N,N'-dimethylformamide (50 ml). Evolution of gas was noted, and the reaction was allowed to stir at room temperature for 18 hours. The mixture was concentrated under reduced pressure and the residual orange oil was dissolved in dichloromethane (300 ml), washed with 0.5M aqueous hydrochloric acid (250 ml) containing methanol (10 ml) and the aqueous phase was separated and extracted with dichloromethane (2×300 ml). The combined organic extracts were washed with brine (300 ml) containing methanol (20 ml), dried over magnesium sulphate, filtered and concentrated under reduced pressure. The residual orange oil was purified by flash chromatography on silica gel eluting with cyclohexane:ethyl acetate (80:20, by volume) to provide the title compound (12.0 g) as an orange oil.

¹H NMR (400 MHz, CDCl₃): δ=1.17 (t, 3H), 2.33 (q, 2H), 2.58 (t, 2H), 3.76 (t, 2H), 4.53 (s, 2H), 5.57 (s, 1H), 7.13 (m, 5H). LRMS (electrospray): m/z [MNa⁺] 257. Microanalysis: Found C, 71.77; H, 7.74. C₁₄H₁₈O₃ requires C, 71.76; H, 7.69%.

Preparation 7

(4E)-1-(Benzyloxy)-4-chloro-5-hydroxy-4-hepten-3-one

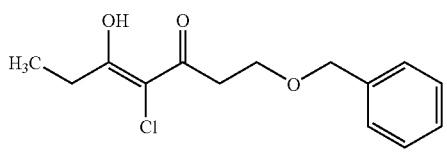

Chlorotrimethylsilane (10 ml, 51.3 mmol) was added to a solution of the enol from Preparation 6 (4.0 g, 17.1 mmol) in acetonitrile (25 ml) under nitrogen at 0° C. Dimethylsulfoxide (3.6 ml, 51.3 mmol) followed by tert-butylammonium bromide (275 mg, 0.85 mmol) were then added and the reaction was stirred at 0° C. for 2 hours. The mixture was diluted with water (100 ml), extracted with diethylether (100 ml) and the organic phase was washed with brine (50 ml), dried over magnesium sulphate and concentrated under reduced pressure. The residual pink oil was purified by flash chromatography on silica gel eluting with cyclohexane:ethyl acetate (80:20, by volume) to provide the title compound (3.76 g) as a pink oil.

¹H NMR (400 MHz, CDCl₃): δ=1.17 (t, 3H), 2.62 (q, 2H), 2.96 (t, 2H), 3.79 (t, 2H), 4.57 (s, 2H), 7.12 (m, 5H), 15.49 (s, 1H). LRMS (electrospray): m/z [MNa⁺] 291.

Preparation 8

5-({(1E)-1-[3-(Benzyloxy)propanoyl]-2-hydroxy-1-butenyl}oxy)isophthalonitrile

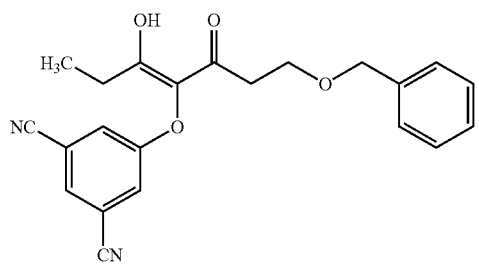

To a stirred solution of the chlorodiketone from Preparation 7 (1.5 g, 5.6 mmol) in acetone (30 ml) was added the phenol from Preparation 3 (0.8 g, 5.6 mmol) followed by cesium carbonate (1.8 g, 5.6 mmol). The reaction mixture was heated at reflux for 2 hours and was then allowed to cool to room temperature. The reaction mixture was concentrated under reduced pressure and the residue was diluted with between water (50 ml), 2N aqueous hydrochloric acid (50 ml) and extracted with dichloromethane (2×100 ml). The combined organic components were dried over magnesium sulfate, filtered and concentrated under reduced pressure. The crude product mixture was purified by column chromatography on silica gel eluting with pentane:ethyl acetate (90:10 then 80:20, by volume) to provide the title compound (0.9 g) as a yellow oil.

¹H NMR (400 MHz, CDCl₃): δ=1.08 (t, 3H), 2.29 (q, 2H), 2.58 (t, 2H), 3.73 (t, 2H), 4.44 (s, 2H), 7.12 (m, 5H, 7.45 (s, 2H), 7.57 (s, 1H), 14.51 (s, 1H). LRMS (atmospheric pressure chemical ionisation): m/z [M–H⁺] 375.

Preparation 9

5-({5-[2-(Benzyloxy)ethyl]-3-ethyl-1H-Pyrazol-4-yl}oxy)isophthalonitrile

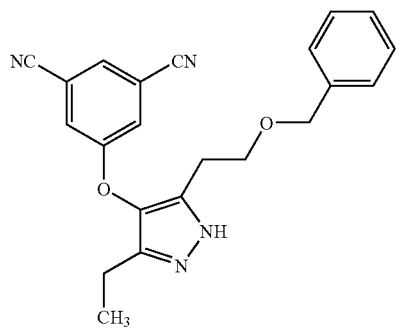

To a stirred solution of the diketone from Preparation 8 (0.85 g, 2.3 mmol) in acetic acid (20 ml) was added hydrazine hydrate (0.17 ml, 3.4 mmol). After 18 hours the reaction mixture was concentrated under reduced pressure to give a yellow oil (0.85 g) which was used without further purification. An analytical sample of the product was purified by preparative HPLC using a Develosil combi-rp C30 50×4.6 mm 3 μm column eluting with a solvent gradient of 5:95 0.1% aqueous trifluoroacetic acid in water:acetonitrile to provide the title compound as a colourless oil.

$^1$H NMR (400 MHz, CDCl$_3$): δ=1.18 (t, 3H), 2.44 (q, 2H), 2.77 (t, 2H), 3.63 (t, 2H), 4.52 (s, 2H), 7.30 (m, 7H), 7.55 (s, 1H). LRMS (electrospray): m/z [MH$^+$] 231, [MNa$^+$] 253.

Preparation 10

5-{[3-Ethyl-5-(2-hydroxyethyl)-1H-pyrazol-4-yl]oxy}isophthalonitrile

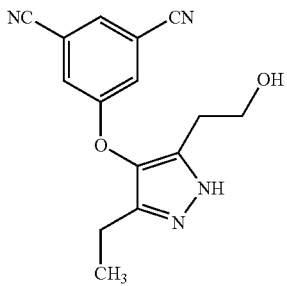

Iron(III)chloride (3.7 g, 23 mmol) was added to a solution of the crude pyrazole from Preparation 9 (0.85 g, 2.3 mmol) in dichloromethane (30 ml) at room temperature. After stirring for 20 minutes the mixture was diluted with dichloromethane (100 ml) and washed with water (50 ml). The separated aqueous phase was washed with dichloromethane (100 ml) and the combined organic components were dried over magnesium sulphate, filtered and concentrated under reduced pressure. The residue was purified by flash chromatography on silica gel eluting with dichloromethane:methanol (98:2 changing to 95:5, by volume) to provide the title compound (0.50 g) as a white solid.

$^1$H NMR (400 MHz, CDCl$_3$): δ=1.19 (t, 3H), 2.51 (q, 2H), 2.69 (t, 2H), 3.88 (t, 2H), 7.40 (s, 2H), 7.59 (s, 1H). LRMS (electrospray): m/z [MH$^+$] 283.

The invention claimed is:

1. A compound of formula (I)

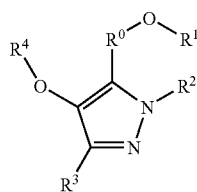

or a pharmaceutically acceptable salt, solvate or derivative thereof, wherein:

$R^0$ is absent or $C_1$–$C_6$ alkylene;

$R^1$ is phenyl substituted by —SO$_y$R$^5$, (C$_1$–C$_6$ alkylene)-SO$_y$R$^5$, —SO$_y$CF$_3$, —(C$_1$–C$_6$ alkylene)-SO$_y$CF$_3$, —CO$_2$R$^5$, —(C$_0$–C$_6$ alkylene)-CO$_2$R$^5$, OCF$_3$, a five or six-membered aromatic heterocyclic group containing (i) from 1 to 4 nitrogen heteroatom(s) or (ii) 1 or 2 nitrogen heteroatom(s) and 1 oxygen or 1 sulphur heteroatom (said heterocyclic group being optionally substituted by halo, oxo, —CN, —COR$^5$, —CO$_2$R$^5$, —CONR$^5$R$^5$, —SO$_y$R$^5$, —SO$_y$CF$_3$, —SO$_2$NR$^5$R$^5$, —NR$^5$SO$_2$R$^5$, —OR$^5$, —OCF$_3$, —NR$^5$R$^5$, —(C$_1$–C$_6$ alkylene)-NR$^5$R$^5$, C$_1$–C$_6$ alkyl, fluoro(C$_1$–C$_6$)alkyl or C$_3$–C$_7$ cycloalkylor); or, when R$^0$ is C$_1$–C$_6$ alkylene, R$^1$ may also be a five or six-membered aromatic heterocyclic group containing (i) from 1 to 4 nitrogen heteroatom(s) or (ii) 1 or 2 nitrogen heteroatom(s) and 1 oxygen or 1 sulphur heteroatom or (iii) 1 or 2 oxygen or sulphur heteroatom(s), said heterocyclic group being optionally substituted by halo, oxo, —CN, —COR$^5$, —CONR$^5$R$^5$, —SO$_2$NR$^5$R$^5$, —NR$^5$SO$_2$R$^5$, —OR$^5$, —OR$^{11}$, —NR$^5$R$^5$, —(C$_1$–C$_6$ alkylene)-NR$^5$R$^5$, R$^7$ or R$^{11}$; said phenyl being optionally additionally substituted by halo, —CN, —COR$^5$, —CONR$^5$R$^5$, —SO$_2$NR$^5$R$^5$, —NR$^5$SO$_2$R$^5$, —OR$^5$, —NR$^5$R$^5$, —(C$_1$–C$_6$ alkylene)-NR$^5$R$^5$, C$_1$–C$_6$ alkyl, halo(C$_1$–C$_6$) alkyl or C$_3$–C$_7$ cycloalkyl;

$R^2$ is H, C$_1$–C$_6$ alkyl, C$_3$–C$_6$ alkenyl, C$_3$–C$_6$ alkynyl, C$_3$–C$_7$ cycloalkyl, C$_3$–C$_7$ cycloalkenyl, phenyl, benzyl, R$^8$ or R$^9$, said C$_1$–C$_6$ alkyl, C$_3$–C$_7$ cycloalkyl, phenyl and benzyl being optionally substituted by halo, —OR$^5$, —OR$^{10}$, —CN, —CO$_2$R$^7$, —OCONR$^5$R$^5$, —CONR$^5$R$^5$, —C(=NR$^5$)NR$^5$OR$^5$, —CONR$^5$NR$^5$R$^5$, —NR$^6$R$^6$, —NR$^5$R$^{10}$, —NR$^5$COR$^5$, —NR$^5$COR$^8$, —NR$^5$COR$^{10}$, —NR$^5$CO$_2$R$^5$, —NR$^5$CONR$^5$R$^5$, —SO$_2$NR$^5$R$^5$, —NR$^5$SO$_2$R$^5$, —NR$^5$SO$_2$NR$^5$R$^5$, R$^8$ or R$^9$;

$R^3$ is H, C$_1$–C$_6$ alkyl, C$_3$–C$_7$ cycloalkyl, phenyl, benzyl, halo, —CN, —OR$^7$, —CO$_2$R$^5$, —CONR$^5$R$^5$, R$^8$ or R$^9$, said C$_1$–C$_6$ alkyl, C$_3$–C$_7$ cycloalkyl, phenyl and benzyl being optionally substituted by halo, —CN, —OR$^5$, —CO$_2$R$^5$, —CONR$^5$R$^5$, —OCONR$^5$R$^5$, —NR$^5$CO$_2$R$^5$, —NR$^6$R$^6$, —NR$^5$COR$^5$, —SO$_2$NR$^5$R$^5$, —NR$^5$CONR$^5$R$^5$, —NR$^5$SO$_2$R$^5$, R$^8$ or R$^9$;

$R^4$ is phenyl, naphthyl or pyridyl, each being optionally substituted by R$^8$, halo, —CN, C$_1$–C$_6$ alkyl, C$_1$–C$_6$ haloalkyl, C$_3$–C$_7$ cycloalkyl, C$_1$–C$_6$ alkoxy, —CONR$^5$R$^5$, OR$^{11}$, SO$_x$R$^6$, O—(C$_1$–C$_6$ alkylene)-CONR$^5$R$^5$, O—(C$_1$–C$_6$ alkylene)-NR$^5$R$^5$, or O—(C$_1$–C$_6$ alkylene)-OR$^6$;

each R$^5$ is independently either H, C$_1$–C$_6$ alkyl or C$_3$–C$_7$ cycloalkyl or, when two R$^5$ groups are attached to the same nitrogen atom, those two groups taken together with the nitrogen atom to which they are attached represent azetidinyl, pyrrolidinyl, piperidinyl, homopiperidinyl, piperazinyl, homopiperazinyl or morpholinyl, said azetidinyl, pyrrolidinyl, piperidinyl, homopiperidinyl, piperazinyl, homopiperazinyl and morpholinyl being optionally substituted by C$_1$–C$_6$ alkyl or C$_3$–C$_7$ cycloalkyl;

each R$^6$ is independently either H, C$_1$–C$_6$ alkyl or C$_3$–C$_7$ cycloalkyl;

R$^7$ is C$_1$–C$_6$ alkyl or C$_3$–C$_7$ cycloalkyl;

R$^8$ is a five or six-membered, aromatic heterocyclic group containing (i) from 1 to 4 nitrogen heteroatom(s) or (ii) 1 or 2 nitrogen heteroatom(s) and 1 oxygen or 1 sulphur heteroatom or (iii) 1 or 2 oxygen or sulphur heteroatom(s), said heterocyclic group being optionally substituted by halo, oxo, —CN, —COR$^5$, —CONR$^5$R$^5$, —SO$_2$NR$^5$R$^5$, —NR$^5$SO$_2$R$^5$, —OR$^5$, —NR⁵R⁵, —(C₁–C₆ alkylene)-NR⁵R⁵, C₁–C₆ alkyl, fluoro(C₁–C₆)alkyl or C₃–C₇ cycloalkyl;

R⁹ is a four to seven-membered, saturated or partially unsaturated heterocyclic group containing (i) 1 or 2 nitrogen heteroatom(s) or (ii) 1 nitrogen heteroatom and 1 oxygen or 1 sulphur heteroatom or (iii) 1 oxygen or sulphur heteroatom, said heterocyclic group being optionally substituted by oxo, C₁–C₆ alkyl, C₃–C₇ cycloalkyl, —SO₂R⁵, —CONR⁵R⁵, —OCOR⁵, —CO—(C₁–C₆ alkylene)-OR⁵ or —COR⁵ and optionally substituted on a carbon atom which is not adjacent to a heteroatom by halo, —OR⁵, —NR⁵R⁵, —NR⁵COR⁵, —NR⁵COOR⁵, —NR⁵CONR⁵R⁵, —NR⁵SO₂R⁵ or —CN;

R¹⁰ is C₁–C₆ alkyl substituted by R⁸, R⁹, —OR⁵, —CONR⁵R⁵, —NR⁵COR⁵ or —NR⁵R⁵;

R¹¹ is phenyl optionally substituted by halo, —CN, —COR⁵, –CONR⁵R⁵, —SO₂NR⁵R⁵, —NR⁵SO₂R⁵, —OR⁵, —NR⁵R⁵, —(C₁–C₆ alkylene)-NR⁵R⁵, C₁–C₆ alkyl, halo(C₁–C₆)alkyl or C₃–C₇ cycloalkyl; and x and y are independently 0, 1 or 2.

2. A pharmaceutical composition comprising a compound according to claim 1 together with one or more pharmaceutically acceptable excipients, diluents or carriers.

3. A pharmaceutical composition according to claim 2 comprising one or more additional therapeutic agents.

4. A method of treating HIV or a resulting acquired immune deficiency syndrome (AIDS), comprising administering an effective amount of a compound of formula (I) accordino to claim 1, or a pharmaceutically acceptable salt or solvate thereof, or a pharmaceutical composition according to claim 2.

5. A method of treating HIV or a resulting acquired immune deficiency syndrome (AIDS), comprising administering an effective amount of a pharmaceutical composition according to claim 3.

6. A process for preparing the compound of formula (I)

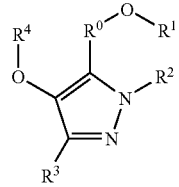

(I)

or a pharmaceutically acceptable salt or solvate thereof, which comprises:

(A) reaction of a compound of formula (V)

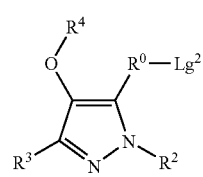

(V)

with an alcohol of formula (IV),

—OH  (IV), under conventional conditions; or (B) reaction of an alcohol of formula (III)

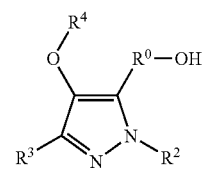

(III)

with a compound of formula (II),

Lg-R¹  (II), under conventional conditions; or (C) reaction of a compound of formula (III) with an alcohol of formula (IV) under dehydrating conditions; or (D) for the preparation of a compound of formula (I)

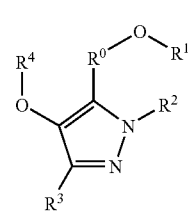

(I)

in which R³ is halo, halogenating a compound of formula (X)

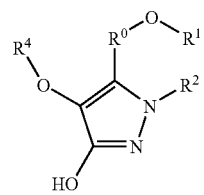

(X)

under conventional conditions, wherein:

each R⁰ is absent or C₁–C₆ alkylene;

each R¹ is phenyl substituted by —SO_yR⁵, (C₁–C₆ alkylene)-SO_yR⁵, —SO_yCF₃, —(C₁–C₆ alkylene)-SO_yCF₃, —CO₂R⁵, —(C₀–C₆ alkylene)-CO₂R⁵, OCF₃, a five or six-membered aromatic heterocyclic group containing (i) from 1 to 4 nitrogen heteroatom(s) or (ii) 1 or 2 nitrogen heteroatom(s) and 1 oxygen or 1 sulphur heteroatom (said heterocyclic group being optionally substituted by halo, oxo, —CN, —COR⁵, —CO₂R⁵, —CONR⁵R⁵, —SO_yR⁵, —SO_yCF₃, —SO₂NR⁵R⁵, —NR⁵SO₂R⁵, —OR⁵, —OCF₃, —NR⁵R⁵, —(C₁–C₆ alkylene)-NR⁵R⁵, C₁–C₆ alkyl, fluoro(C₁–C₆)alkyl or C₃–C₇ cycloalkylor); or, when R⁰ is C₁–C₆ alkylene, R¹ may also be a five or six-membered aromatic heterocyclic group containing (i) from 1 to 4 nitrogen heteroatom(s) or (ii) 1 or 2 nitrogen heteroatom(s) and 1 oxygen or 1 sulphur heteroatom or (iii) 1 or 2 oxygen or sulphur heteroatom(s), said heterocyclic group being optionally substituted by halo, oxo, —CN, —COR⁵, —CONR⁵R⁵, —SO₂NR⁵R⁵, —NR⁵SO₂R⁵, —OR⁵, —OR¹¹, —NR⁵R⁵, —(C₁–C₆ alkylene)-NR⁵R⁵, R⁷ or $R^{11}$; said phenyl being optionally additionally substituted by halo, —CN, —COR$^5$, —CONR$^5$R$^5$, —SO$_2$NR$^5$R$^5$, —NR$^5$SO$_2$R$^5$, —OR$^5$, —NR$^5$R$^5$, —(C$_1$–C$_6$ alkylene)-NR$^5$R$^5$, C$_1$–C$_6$ alkyl, halo(C$_1$–C$_6$) alkyl or C$_3$–C$_7$ cycloalkyl;

each $R^2$ is H, C$_1$–C$_6$ alkyl, C$_3$–C$_6$ alkenyl, C$_3$–C$_6$ alkynyl, C$_3$–C$_7$ cycloalkyl, C$_3$–C$_7$ cycloalkenyl, phenyl, benzyl, $R^8$ or $R^9$, said C$_1$–C$_6$ alkyl, C$_3$–C$_7$ cycloalkyl, phenyl and benzyl being optionally substituted by halo, —OR$^5$, —OR$^{10}$, —CN, —CO$_2$R$^7$, —OCONR$^5$R$^5$, —CONR$^5$R$^5$, —C(=NR$^5$)NR$^5$OR$^5$, —CONR$^5$NR$^5$R$^5$, —NR$^6$R$^6$, —NR$^5$R$^{10}$, —NR$^5$COR$^5$, —NR$^5$COR$^8$, —NR$^5$COR$^{10}$, —NR$^5$CO$_2$R$^5$, —NR$^5$CONR$^5$R$^5$, —SO$_2$NR$^5$R$^5$, —NR$^5$SO$_2$R$^5$, —NR$^5$SO$_2$NR$^5$R$^5$, $R^8$ or $R^9$;

each $R^3$ is H, C$_1$–C$_6$ alkyl, C$_3$–C$_7$ cycloalkyl, phenyl, benzyl, halo, —CN, —OR$^7$, —CO$_2$R$^5$, —CONR$^5$R$^5$, $R^8$ or $R^9$, said C$_1$–C$_6$ alkyl, C$_3$–C$_7$ cycloalkyl, phenyl and benzyl being optionally substituted by halo, —CN, —OR$^5$, —CO$_2$R$^5$, —CONR$^5$R$^5$, —OCONR$^5$R$^5$, —NR$^5$CO$_2$R$^5$, —NR$^6$R$^6$, —NR$^5$COR$^5$, —SO$_2$NR$^5$R$^5$, —NR$^5$CONR$^5$R$^5$, —NR$^5$SO$_2$R$^5$, $R^8$ or $R^9$;

each $R^4$ is phenyl, naphthyl or pyridyl, each being optionally substituted by $R^8$, halo, —CN, C$_1$–C$_6$ alkyl, C$_1$–C$_6$ haloalkyl, C$_3$–C$_7$ cycloalkyl, C$_1$–C$_6$ alkoxy, —CONR$^5$R$^5$, OR$^{11}$, SO$_x$R$^6$, O—(C$_1$–C$_6$ alkylene)-CONR$^5$R$^5$, O—(C$_1$–C$_6$ alkylene)-NR$^5$R$^5$, or O—(C$_1$–C$_6$ alkylene)-OR$^6$;

each $R^5$ is independently either H, C$_1$–C$_6$ alkyl or C$_3$–C$_7$ cycloalkyl or, when two $R^5$ groups are attached to the same nitrogen atom, those two groups taken together with the nitrogen atom to which they are attached represent azetidinyl, pyrrolidinyl, piperidinyl, homopiperidinyl, piperazinyl, homopiperazinyl or morpholinyl, said azetidinyl, pyrrolidinyl, piperidinyl, homopiperidinyl, piperazinyl, homopiperazinyl and morpholinyl being optionally substituted by C$_1$–C$_6$ alkyl or C$_3$–C$_7$ cycloalkyl;

each $R^6$ is independently either H, C$_1$–C$_6$ alkyl or C$_1$–C$_7$ cycloalkyl;

each $R^7$ is C$_1$–C$_6$ alkyl or C$_3$–C$_7$ cycloalkyl;

each $R^8$ is a five or six-membered, aromatic heterocyclic group containing (i) from 1 to 4 nitrogen heteroatom(s) or (ii) 1 or 2 nitrogen heteroatom(s) and 1 oxygen or 1 sulphur heteroatom or (iii) 1 or 2 oxygen or sulphur heteroatom(s), said heterocyclic group being optionally substituted by halo, oxo, —CN, —COR$^5$, —CONR$^5$R$^5$, —SO$_2$NR$^5$R$^5$, —NR$^5$SO$_2$R$^5$, —OR$^5$, —NR$^5$R$^5$, —(C$_1$–C$_6$ alkylene)-NR$^5$R$^5$, C$_1$–C$_6$ alkyl, fluoro(C$_1$–C$_6$)alkyl or C$_3$–C$_7$ cycloalkyl;

each $R^9$ is a four to seven-membered, saturated or partially unsaturated heterocyclic group containing (i) 1 or 2 nitrogen heteroatom(s) or (ii) 1 nitrogen heteroatom and 1 oxygen or 1 sulphur heteroatom or (iii) 1 oxygen or sulphur heteroatom, said heterocyclic group being optionally substituted by oxo, C$_1$–C$_6$ alkyl, C$_3$–C$_7$ cycloalkyl, —SO$_2$R$^5$, —CONR$^5$R$^5$, —COOR$^5$, —CO—(C$_1$–C$_6$ alkylene)-OR$^5$ or —COR$^5$ and optionally substituted on a carbon atom which is not adjacent to a heteroatom by halo, —OR$^5$, —NR$^5$R$^5$, —NR$^5$COR$^5$, —NR$^5$COOR$^5$, —NR$^5$CONR$^5$R$^5$, —NR$^5$SO$_2$R$^5$ or —CN;

each $R^{10}$ is C$_1$–C$_6$ alkyl substituted by $R^8$, $R^9$, —OR$^5$, —CONR$^5$R$^5$, —NR$^5$COR$^5$ or —NR$^5$R$^5$;

each $R^{11}$ is phenyl optionally substituted by halo, —CN, —COR$^5$, —CONR$^5$R$^5$, —SO$_2$NR$^5$R$^5$, —NR$^5$SO$_2$R$^5$, —OR$^5$, —NR$^5$R$^5$, —(C$_1$–C$_6$ alkylene)-NR$^5$R$^5$, C$_1$–C$_6$ alkyl, halo(C$_1$–C$_6$)alkyl or C$_3$–C$_7$ cycloalkyl;

x and y are independently 0, 1 or 2;

Lg is sulphonyl chloride; and

Lg$^2$ is a sulphonic ester group.

\* \* \* \* \*